United States Patent
Torres

(10) Patent No.: US 10,357,290 B2
(45) Date of Patent: Jul. 23, 2019

(54) APPARATUS AND METHOD FOR CONNECTING SURGICAL RODS

(71) Applicant: Alphatec Spine, Inc., Carlsbad, CA (US)

(72) Inventor: Eller Torres, Carlsbad, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 242 days.

(21) Appl. No.: 14/798,749

(22) Filed: Jul. 14, 2015

(65) Prior Publication Data

US 2015/0327890 A1 Nov. 19, 2015

Related U.S. Application Data

(63) Continuation of application No. 13/569,312, filed on Aug. 8, 2012, now Pat. No. 9,107,703.

(60) Provisional application No. 61/604,333, filed on Feb. 28, 2012, provisional application No. 61/527,199, filed on Aug. 25, 2011.

(51) Int. Cl.
*A61B 17/70* (2006.01)

(52) U.S. Cl.
CPC ...... *A61B 17/7049* (2013.01); *A61B 17/7052* (2013.01)

(58) Field of Classification Search
CPC .............. A61B 17/7049; A61B 17/705; A61B 17/7052; A61B 17/7043
See application file for complete search history.

(56) References Cited

U.S. PATENT DOCUMENTS

| | | | | |
|---|---|---|---|---|
| 6,273,914 | B1* | 8/2001 | Papas | A61B 17/7007 623/17.11 |
| 8,292,924 | B2* | 10/2012 | Neary | A61B 17/7052 606/250 |
| 8,864,799 | B2* | 10/2014 | Kraus | A61B 17/7049 606/253 |
| 2007/0225713 | A1* | 9/2007 | Altarac | A61B 17/7052 606/64 |
| 2008/0109039 | A1* | 5/2008 | Michielli | A61B 17/7052 606/251 |

(Continued)

OTHER PUBLICATIONS

Kraus, WO 2011/069963 A2, International Publication date Jun. 16, 2011.*

(Continued)

*Primary Examiner* — Ellen C Hammond
*Assistant Examiner* — Tessa M Matthews
(74) *Attorney, Agent, or Firm* — Honigman LLP

(57) ABSTRACT

An exemplary apparatus for connecting surgical rods according the principles of the present disclosure includes an elongate first arm, an elongate second arm, and a clamping assembly. The elongate first arm includes a first end that couples with a first rod and a second end with a first engagement portion. The elongate second arm includes a first end that couples with a second rod and a second end terminating in a second engagement portion. The clamping assembly includes a passageway that slidably receives the first engagement portion and that retains the second engagement portion and an adjustment member offset from the passageway that adjusts a clamping force to restrict positioning of the second engagement portion relative to the first engagement portion.

16 Claims, 12 Drawing Sheets

(56) References Cited

U.S. PATENT DOCUMENTS

2012/0226313 A1* 9/2012 Dace .................. A61B 17/7068
606/248

OTHER PUBLICATIONS

Machine Translatation of WO 2011/069963 A2 Description, generated via Espacenet, publication date Jun. 16, 2011.*

* cited by examiner

APPARATUS AND METHOD FOR CONNECTING SURGICAL RODS

CROSS REFERENCE TO RELATED APPLICATIONS

The present application is a continuation of U.S. application Ser. No. 13/569,312 filed on Aug. 8, 2012 and which claims priority to U.S. Provisional App. Ser. No. 61/527,199 filed on Aug. 25, 2011, entitled "Apparatus and Method for Connecting Surgical Rods" and U.S. Provisional App. Ser. No. 61/604,333 filed on Feb. 28, 2012, also entitled "Apparatus and Method for Connecting Surgical Rods."

FIELD

The present invention relates generally to the field of surgery, and more specifically, to an apparatus and method for connecting surgical rods.

BACKGROUND

One of the goals of a spinal fusion procedure is to unite two or more vertebrae to prevent them from moving independently of each other. This may be done to improve posture, increase ability to ventilate the lungs, prevent pain, or treat spinal instability and reduce the risk of nerve damage. According to the American Academy of Orthopedic Surgeons, approximately a quarter-million spinal fusions are performed each year, half on the upper and half on the lower spine.

Posterior spinal fusion surgery involves approaching the patient from the back of patient, as opposed to anterior or lateral spinal fusion through the abdomen or side. There are three know posterior fusion techniques (all three are typically performed with pedicle screw fixation). There have been various approaches and systems for performing posterior spinal surgery. Some conventional systems further include titanium construction that is compatible with current CT and MRI scanning technology, low profile implant systems, top-loading and top-tightening systems, and other parameters. Some systems also include cross-connectors that allow one-piece implant to be applied to a dual-rod construct for a top-loading approach.

Conventional devices and systems for linking rods have a number of disadvantages. Many cross-connectors do not provide sufficient flexibility when adjusting the devices either prior to, during, or after their placement into the patient. Alternatively, many cross-connectors have grown too complex with multiple parts, joints, and locking set screws. Thus, these devices force a surgeon to utilize a specific configuration, leaving very little room for adjustment in accordance with patient's physiological characteristics and needs. Further, these devices do not allow a surgeon to connect multiple rods by actuating a single setscrew mechanism.

SUMMARY

An exemplary apparatus for connecting surgical rods according the principles of the present disclosure includes an elongate first arm, an elongate second arm, and a clamping assembly. The elongate first arm includes a first end that couples with a first rod and a second end with a first engagement portion. The elongate second arm includes a first end that couples with a second rod and a second end terminating in a second engagement portion. The clamping assembly includes a passageway that slidably receives the first engagement portion and that retains the second engagement portion and an adjustment member offset from the passageway that adjusts a clamping force to restrict positioning of the second engagement portion relative to the first engagement portion.

In other features, the first engagement portion includes a first recessed portion extending along a longitudinal length of the first arm. The second engagement portion includes a spherical portion configured to pivot and translate within the first engagement portion. The second engagement portion comprises a first hemispherical portion with a first radius and a second hemispherical portion with a second radius greater than the first radius. The passageway includes a second recessed portion that receives the second engagement portion and permits pivoting of the second engagement portion within the clamping assembly. An aperture extends through the clamping assembly adjacent to the passageway. The clamping assembly includes an upper portion, a side portion, and a lower portion that form a generally C-shaped clamping member.

Another exemplary apparatus for connecting surgical rods according to the principles of the present disclosure includes an elongate first arm, an elongate second arm, and a clamping assembly. The elongate first arm includes a first end that couples with a first rod and a second end with a recessed portion extending along a longitudinal length. The elongate second arm includes a first end that couples with a second rod and a second end terminating in a spherical portion. The clamping assembly extends around the first and second arms and retains the spherical portion within the recessed portion and provides clamping force to control positioning of the first arm relative to the second arm.

In other features, the recessed portion includes a curved channel with a first radius. The spherical portion comprises a first hemispherical portion with a first radius and a second hemispherical portion with a second radius greater than the first radius. The second arm further comprises a pair of flat surfaces adjacent the spherical portion that engage the clamping member to restrict rotation about a longitudinal axis of the second arm. The clamping assembly includes a setscrew that engages the spherical portion and applies a force to clamp the spherical portion and the recessed portion together. The second arm translates along a longitudinal axis of the first arm. The second arm rotates about a longitudinal axis of the second arm relative to the clamping member. The second arm pivots about a transverse axis extending through the spherical portion that is perpendicular to a longitudinal axis of the second arm.

Another exemplary apparatus for connecting surgical rods according the principles of the present disclosure includes a first arm, a second arm, and a collar. The first arm includes a first end formed into a first hook that secures to a first rod and a second elongated end including a channel that extends along a longitudinal length. The second arm includes a first end formed into a second hook that secures to a second rod and second elongated end terminating in a spherical portion. The collar includes a passageway that retains the spherical portion within the channel and that receives a force adjustment member to adjust a clamping force on the spherical portion to allow positioning of the second arm relative to the first arm in a first configuration and to restrict positioning of the first arm relative to the second arm in a second configuration.

In other features, the spherical portion comprises a first hemispherical portion with a first radius that corresponds to a radius of a recessed portion within the passageway and a second hemispherical portion with a second radius that corresponds to a radius of the channel. The second arm translates freely along a longitudinal axis of the first arm in the first configuration. The second arm rotates freely about a longitudinal axis of the second arm in the first configuration. The second arm pivots about a transverse axis extending perpendicular to a longitudinal axis of the first arm in the first configuration.

DETAILED DESCRIPTION

Figure 1:
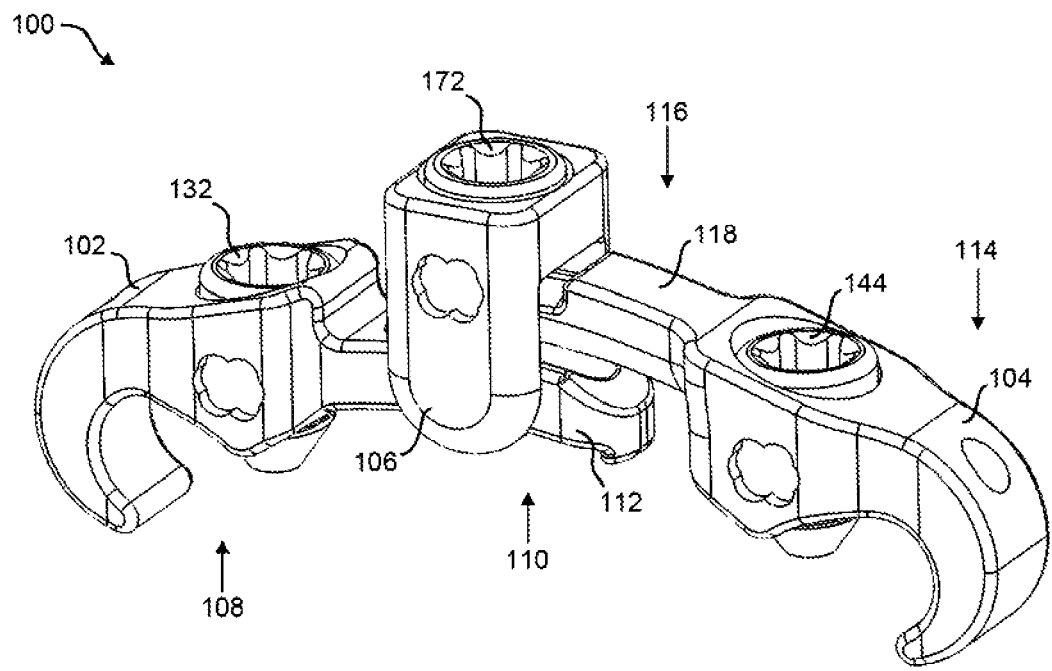
FIGS. 1 and 2 are perspective views of an exemplary apparatus for connecting surgical rods according to the principles of the present disclosure.

The exemplary embodiments of the present invention include two arms with fixed hooks that couple to the alignment rods and a single central link between opposite ends of the two arms provides six degrees of freedom of movement. The six degrees of freedom include rotation and translation along three Cartesian axes passing through the central link. The axes may be described with respect to the sagittal, coronal, and transverse planes of the human anatomy. In some examples, axes normal to these planes may be referred to as the sagittal, coronal, and transverse axes. The sagittal and coronal axes may lie perpendicular to one another in the transverse plane. The transverse and sagittal axes may lie perpendicular to one another in the coronal plane. The coronal and transverse axes may lie perpendicular to one another in the sagittal plane.

The apparatus may generally include a pair of arms, each including a hook at its outer end for attachment to spinal rods extending in the cephalad-caudal direction. The arms extend generally transverse to the spinal rods along their longitudinal axes. The longitudinal axes extend generally parallel to a transverse plane of the body. Each of the pair of arms includes coupling features or engagement portions at its inner end secured by a clamping assembly. For example, the apparatus may include a first arm including a first end that couples with a first rod and a second end with an engagement portion and a second arm including a first end that couples with a second rod and a second end terminating in a spherical head. The central portion of the apparatus may include a collar assembly that allows positioning of the semi-spherical head in the engagement portion in a first configuration and restricts positioning of the semi-spherical head in the engagement portion in a second configuration.

The exemplary embodiments of the present invention are advantageous over the prior art because the apparatus provides greater flexibility for implant adjustment in situ while reducing the number of parts in the assembly. The greater flexibility may provide better fit between the alignment rods and reduce surgery time. The reduced number of parts may decrease likelihood of part failures, reduce costs of manufacturing, and simplify the implantation procedure.

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein. The words proximal and distal are applied herein to denote specific ends of components of the instrument described herein. A proximal end refers to the end of an instrument nearer to an operator of the instrument when the instrument is being used. A distal end refers to the end of a component further from the operator and extending towards the surgical area of a patient and/or the implant.

Figure 2:
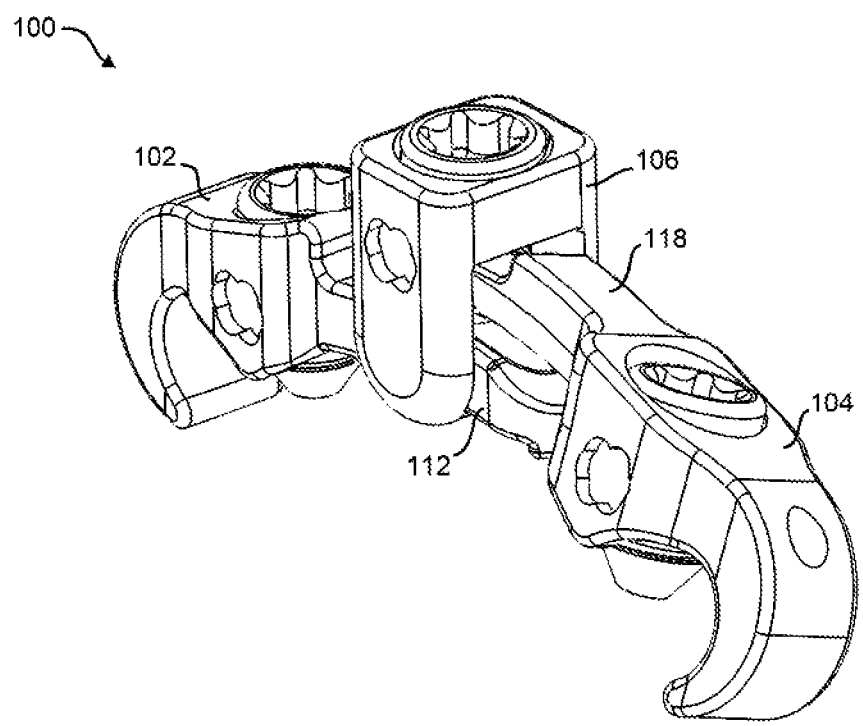

Referring now to FIG. 1, an exemplary crosslink apparatus 100 for connecting surgical alignment rods includes a first arm 102 and a second arm 104 coupled by a collar 106. The first arm 102 includes a first end 108 configured to couple with a first alignment rod (not shown) and a second end 110 with a first engagement portion 112. The second arm 104 includes a first end 114 configured to couple with a second alignment rod (not shown) and a second end 116 with a second engagement portion 118. The collar 106 includes features that allow positioning of the first engagement portion 112 relative to the second engagement portion 118 in a first configuration and restricts positioning of the first engagement portion 112 relative to the second engagement portion 118 in a second configuration. For example, in FIG. 1, the collar 106 may fit snugly around the first and second engagement portions 112 and 118 to sufficiently lock the first arm 102 in position relative to the second arm 104. In FIG. 2, the collar 106 may fit loosely around the first and second engagement portions 112 and 118 to enable free translation of the first arm 102 relative to the second arm 104 and the collar 106 and free rotation of the second arm 104 relative to the first arm 102 and the collar 106.

Figure 3:
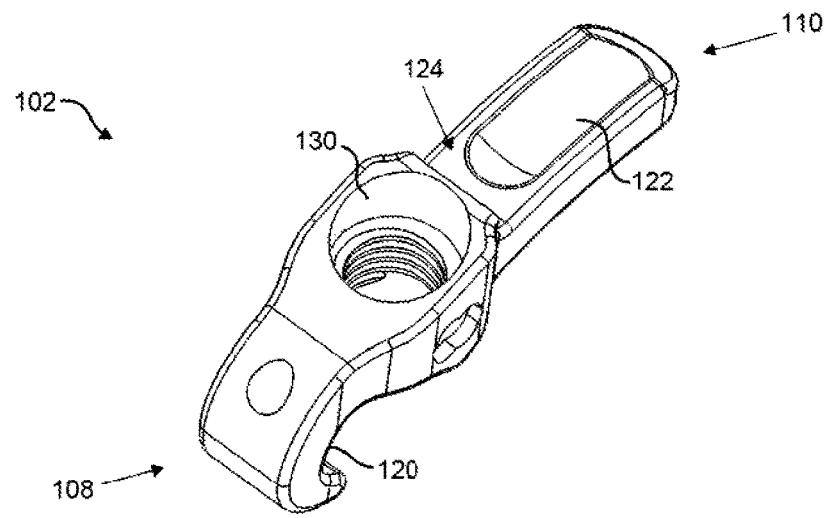
FIGS. 3-5 illustrate an exemplary first arm of the apparatus according to the principles of the present disclosure.
Figure 4:
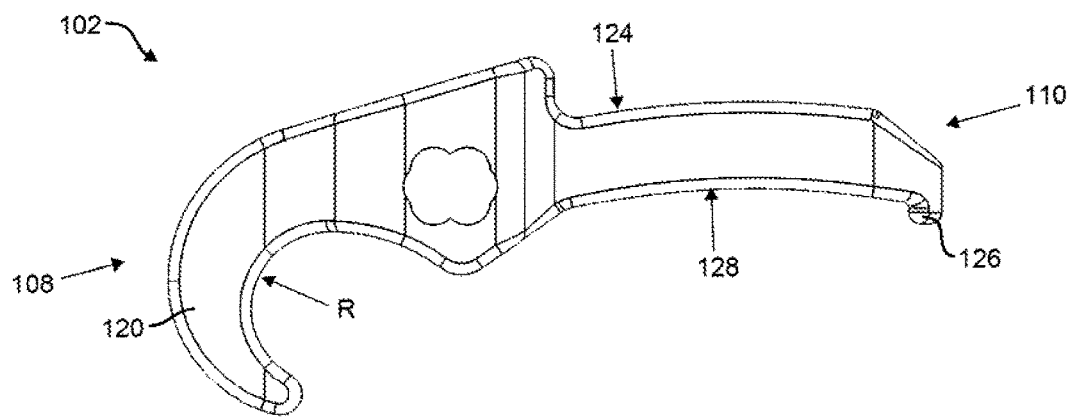
Figure 5:
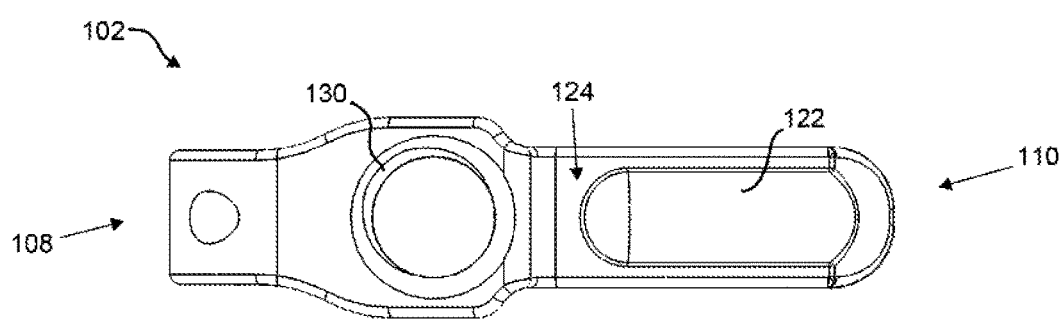
Figure 14:
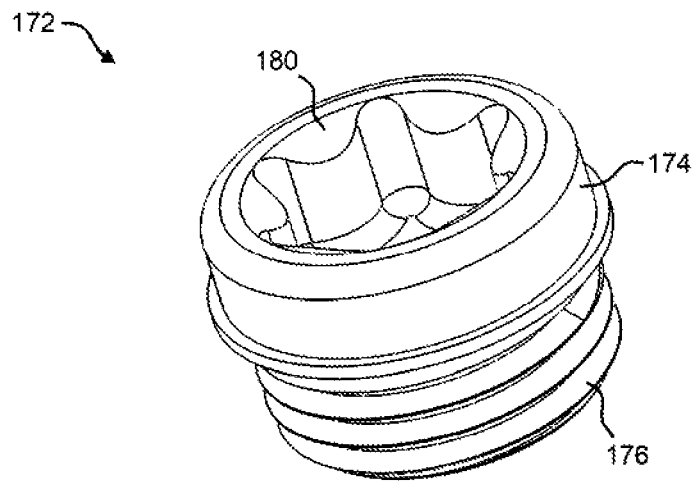
FIGS. 14 and 15 illustrate another exemplary setscrew for use with the collar according to the principles of the present disclosure.
Figure 15:
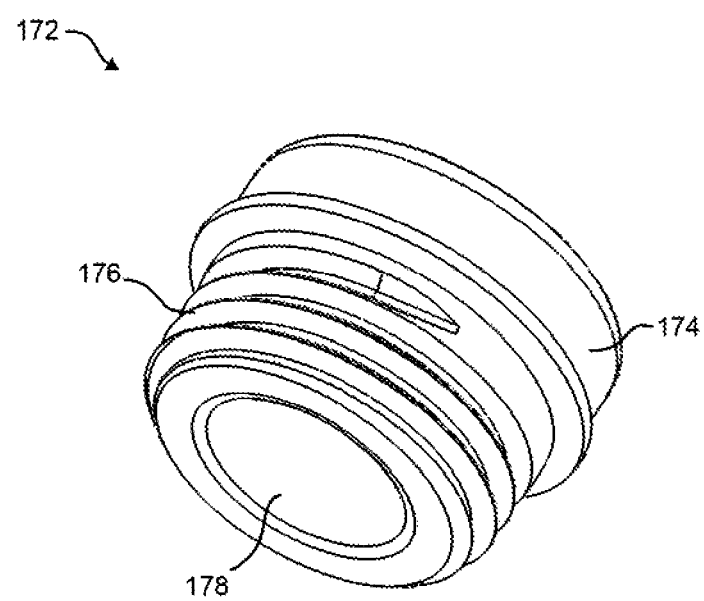

Referring to FIGS. 3-5, additional features of the first arm 102 are illustrated in greater detail. At the first end 108, the first arm 102 may terminate in a first hook 120. The first hook 120 may include a radius R corresponding to the radius or diameter of the first alignment rod. At the second end 110, the engagement portion 112 may include a channel 122 on an upper surface 124. The second end 110 may further include a lip 126 that extends away from a lower surface 128 of the first arm 102. The lip 126 may prevent the first arm 102 from sliding out of the collar 106 after installation. For example, the lower surface 128 may be substantially flat to allow sliding engagement between the engagement portion 112 and the collar 106. As the first end 108 slides away from the collar assembly 106, the lip 126 may contact an outer edge of the collar 106. A first aperture 130 may pass through a portion of the first end 108. The first aperture 130 may receive a first setscrew 132 (shown in FIGS. 1, 14, and 15) that locks the first hook 120 with the first alignment rod (not shown).

Figure 6:
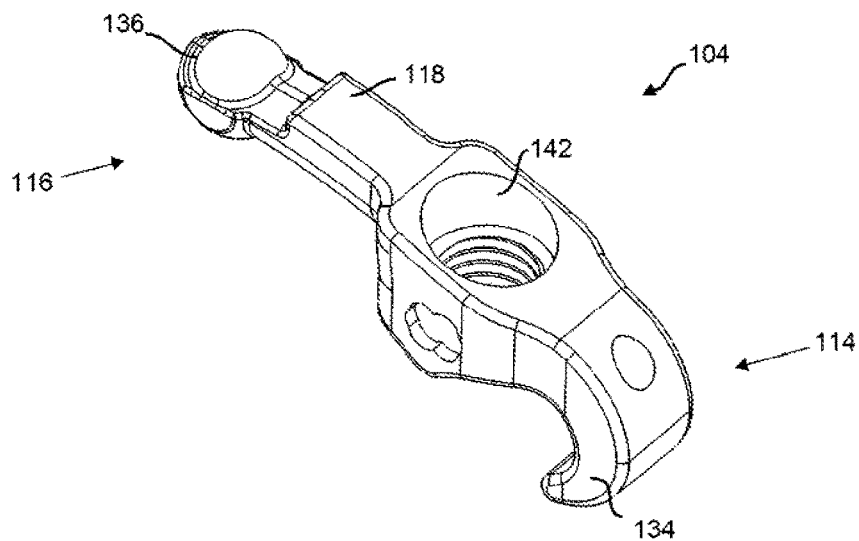
FIGS. 6-8 illustrate an exemplary second arm of the apparatus according to the principles of the present disclosure.
Figure 7:
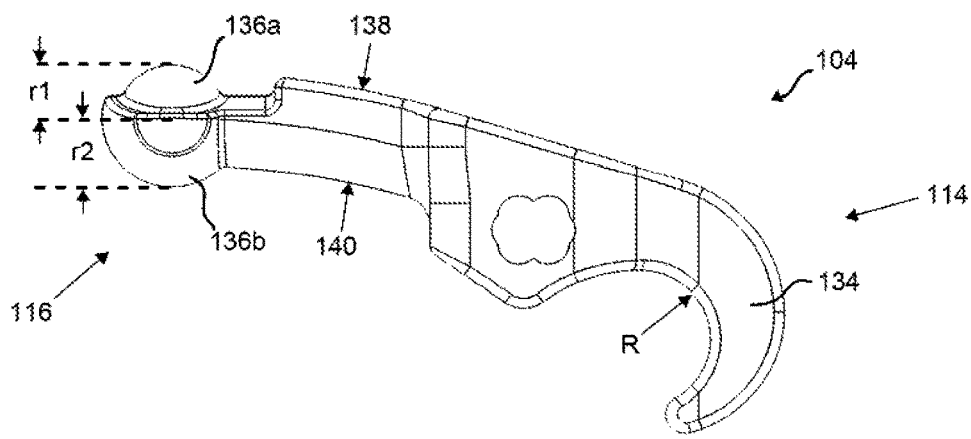
Figure 8:
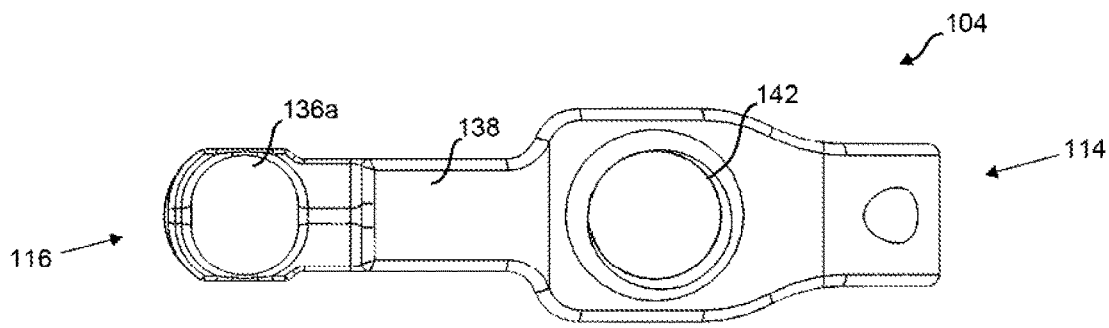

Referring to FIGS. 6-8, additional features of the second arm 104 are illustrated in greater detail. At the first end 114, the second arm 104 may terminate in a second hook 134. The second hook 134 may include a radius R corresponding to the radius or diameter of the second alignment rod. At the second end 116, the second engagement portion 118 may terminate in a head 136. The head 136 may include a first portion 136a and a second portion 136b. The first portion 136a may extend from an upper surface 138 of the second engagement portion 118 and the second portion 136b may extend from a lower surface 140 of the second engagement portion 118. The first portion 136a may include a semi-spherical shape with a first radius R1 and the second portion 136b may include a semi-spherical shape with a second radius R2. The head 136 may be configured to engage the channel 122 of the first arm 102. For example, the channel 122 may include a routed portion of the upper surface 124 having a radius substantially similar to one of the first and second radii R1 and R2. A second aperture 142 may pass through a portion of the first end 114. The second aperture 142 may receive a second setscrew 144 (shown in FIG. 1) that locks the second hook 134 with the second alignment rod (not shown). The second setscrew 144 may be substantially similar to the first setscrew 132.

Figure 9:
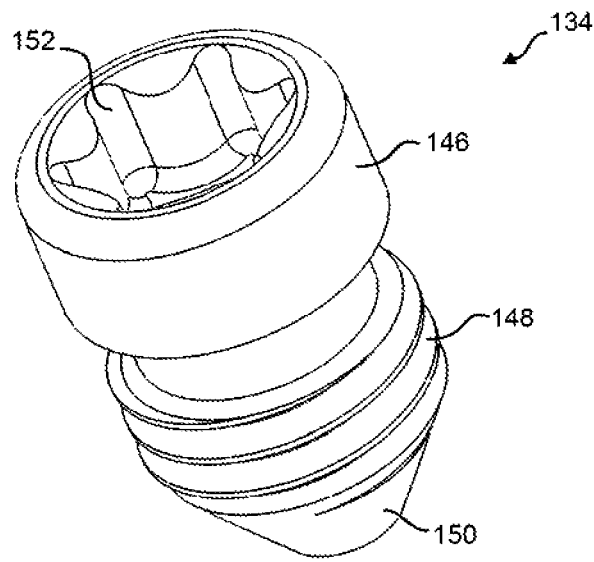
FIGS. 9 and 10 illustrate an exemplary setscrew for use with the first and second arms according to the principles of the present disclosure.
Figure 10:
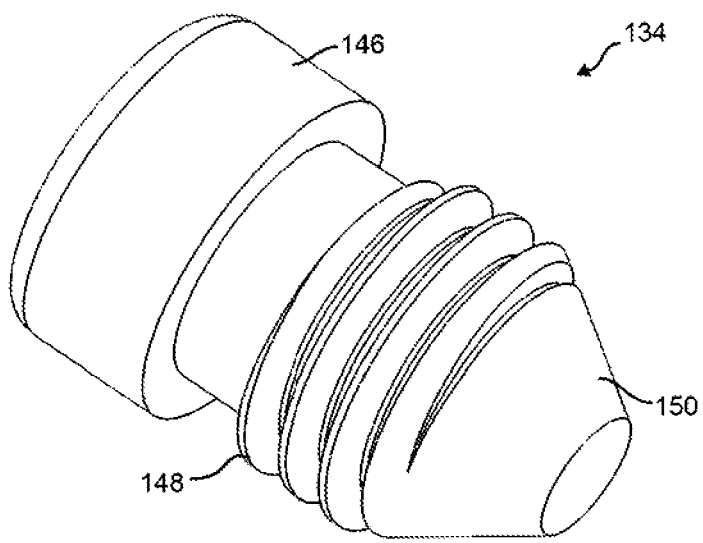

FIGS. 9-10 illustrate additional features of the first setscrew 134 (and second setscrew 144) that enable coupling with surgical rods. The setscrew 132 includes a head portion 146, a threaded portion 148, and a tapered end portion 150. The head portion 146 includes a driving feature 152 for receiving a screwdriver or other tool that may advance the threaded portion 148 relative to a corresponding threading within the aperture 132. The tapered portion 150 may include a straight tapered edge or alternatively a contoured edge (not shown) for engagement with a surgical rod. The tapered portion 150 may engage the surgical rod and force the rod into contact with the first hook 120. The second setscrew 144 may include similar features and similarly engage a second surgical rod and force the second rod into contact with the second hook 134.

Figure 11:
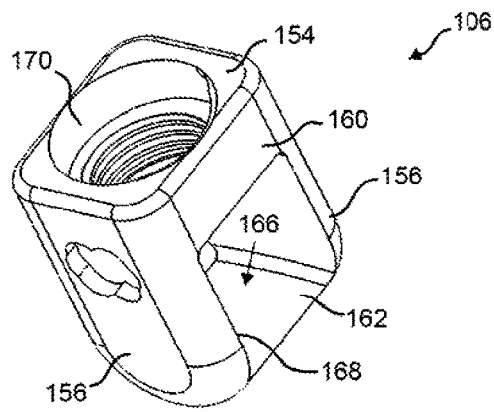
FIGS. 11-13 illustrate an exemplary collar of the apparatus according to the principles of the present disclosure.
Figure 12:
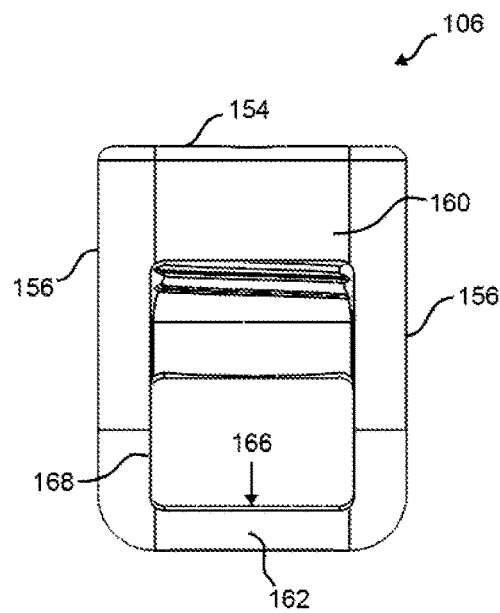
Figure 13:
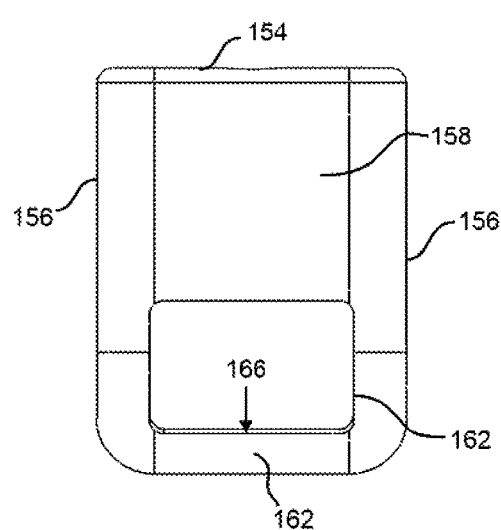

Referring now to FIGS. 11-13, the collar 106 includes features that enable sliding engagement with the first arm 102 and rotational engagement with the second arm 104. The collar 106 includes an upper portion 154, side portions 156, first and second sagittal portions 158 and 160, and a lower portion 162 that together form a substantially cuboidal construct. The first sagittal portion 158 includes a first opening 164 for receiving the first arm 102. For example, the second end 110 of the first arm 102 may be inserted through the first opening 164 and the lower surface 128 may slidably engage an interior surface 166 of the lower portion 162. The second sagittal portion 160 includes a second opening 168 for receiving the first arm 102 and the second arm 104. For example, the second end 118 of the second arm 104 may be inserted through the second opening 168. The second end 110 of the first arm 102 may pass through the interior of the collar 106 and exit through the second opening 168. The lip 126 on the second end 110 may prevent the first arm 102 from sliding out of the collar 106.

The upper portion 154 may include a third aperture 170 extending to the interior of the collar 106. The third aperture 170 may receive a third setscrew 172, shown in FIGS. 1, 14, and 15, for selectively locking the second ends 110 and 118 of the arms 102 and 104 respectively. The setscrew 172 includes a head portion 174, a threaded portion 176, and a recessed portion 178. The head portion 174 includes a driving feature 180 for receiving a screwdriver or other tool that may advance the threaded portion 176 relative to a corresponding threading within the aperture 170. The recessed portion 178 may include concave section having radius similar to the radius R1 of the semispherical head 136a. The end portion 170 may include a conical shaped section configured to receive the semispherical head 136a.

Figure 16:
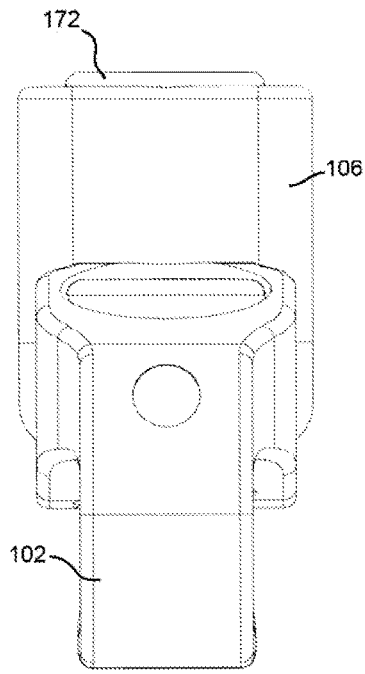
FIGS. 16 and 17 are elevational side views of the exemplary apparatus illustrating rotational movement of the second arm relative to the first arm and the collar according to the principles of the present disclosure.
Figure 17:
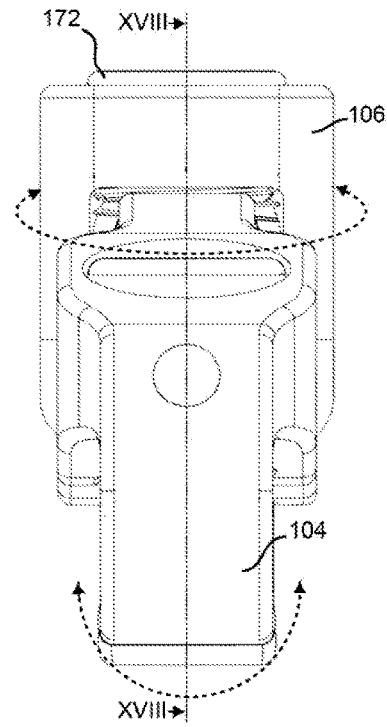
Figure 18:
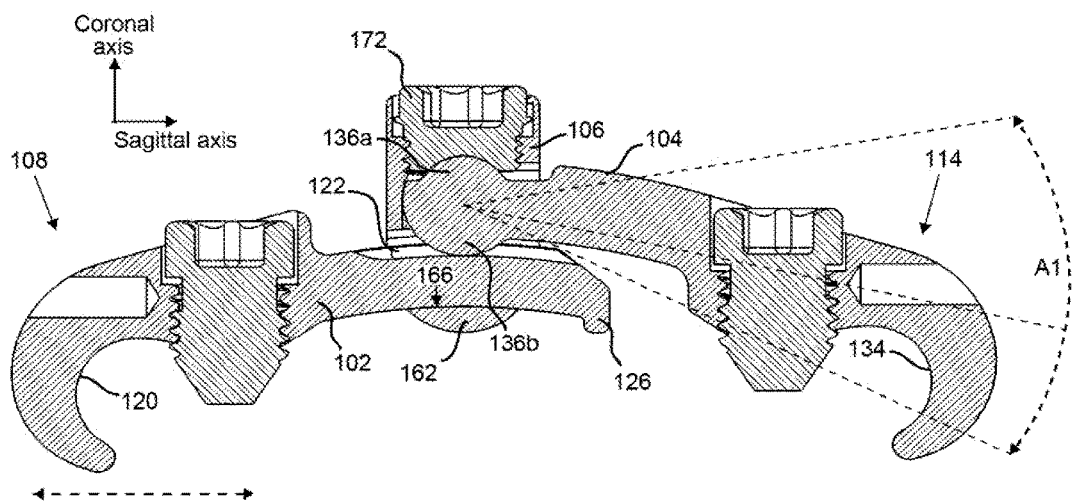
FIG. 18 is a cross-sectional view of the exemplary apparatus according to the principles of the present disclosure illustrating translational and rotational movement of the first and second arms.

FIGS. 16 and 17 illustrate side views of the crosslink 100 looking into the first arm 102 and the second arm 104 respectively. FIG. 18 illustrates a cross-section of the crosslink 100 along the plane XVIII of FIG. 17. The central setscrew 172 engages the upper first portion 136a of the head 136. The lower second portion 136b of the head 136 engages the channel 122. The channel 122 engages interior surface 166 of the lower portion 162 of the collar 106. When the setscrew 172 is loosened, the first arm 102 may slide inside the collar 106 and the second arm 104 may rotate inside the collar 106. As the setscrew 172 is tightened, the first arm 102 may be locked against the second arm 104 within the collar 106. The first arm 102 may slide a distance D in a direction substantially parallel to a sagittal axis of the body. The second arm 104 may rotate about the head 136 in the transverse plane, the sagittal plane, and the coronal plane.

Figure 19:
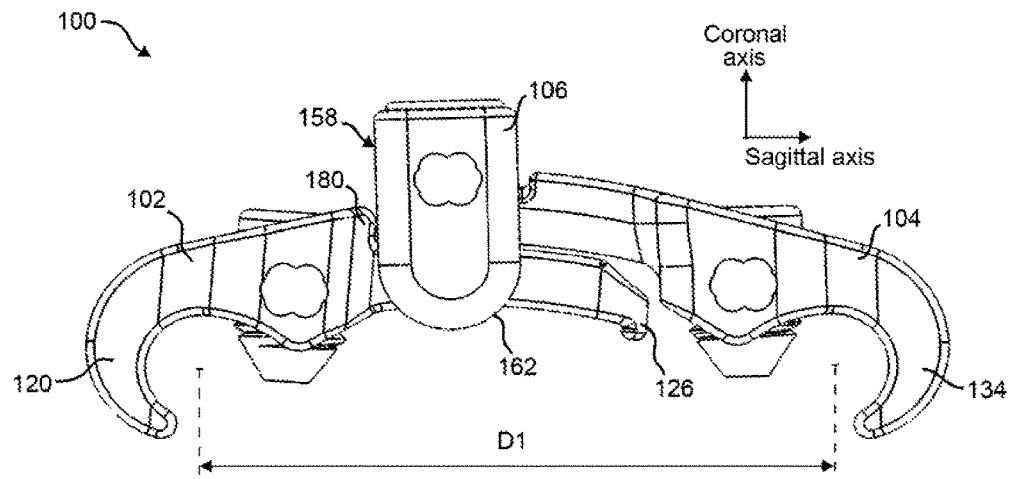
FIGS. 19 and 20 illustrate translational movement of the first arm relative to the second arm and the collar according to the principles of the present disclosure.
Figure 20:
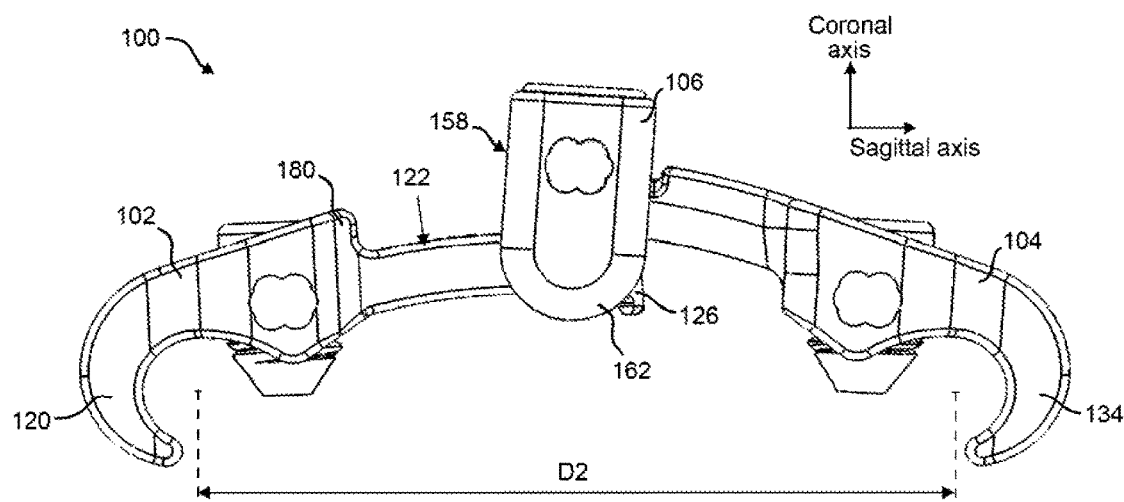

Referring now also to FIGS. 19 and 20, translation of the first arm 102 relative to the second arm 104 and collar 106 in the transverse plane is shown. The first arm 102 may slide within the collar 106 while the head 136 of the second arm 104 rests within the channel 122. Thus, the overall length of the crosslink 100 may vary between a first length D1 and a second length D2 measured from the radial center of the first hook 120 and the second hook 134. The travel of the first arm 102 may be limited by a stop 180 on the first end 108 and the lip 126 on the second end 110. The stop 180 may engage the first transverse portion 158 when the crosslink 100 includes the first length D1. The lip may engage the lower portion 162 when the crosslink 100 includes the second length D2. Therefore, the overall length of the crosslink 100 may be limited in the transverse plane by the lip 126 and the stop 180.

Figure 21:
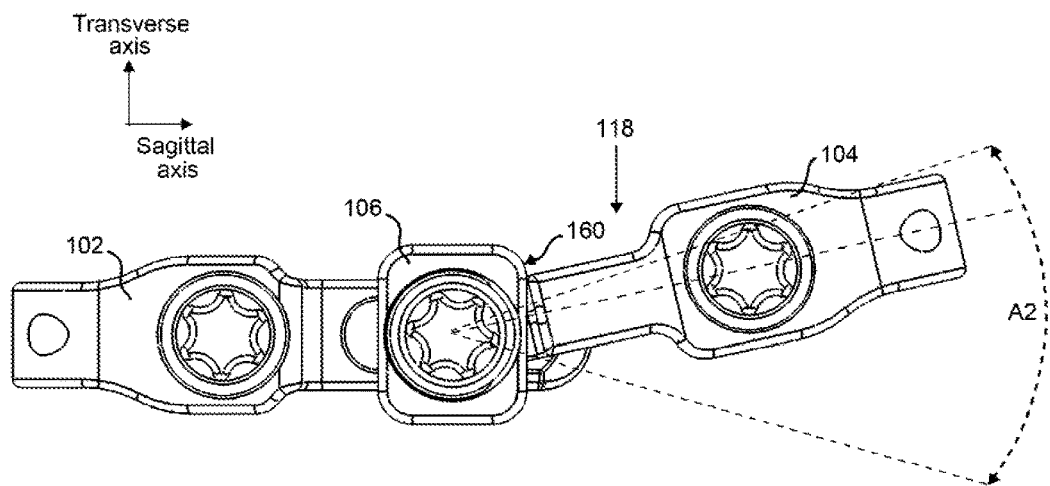
FIGS. 21-24 illustrate rotational movement of the second arm relative to the first arm and the collar according to the principles of the present disclosure.
Figure 22:
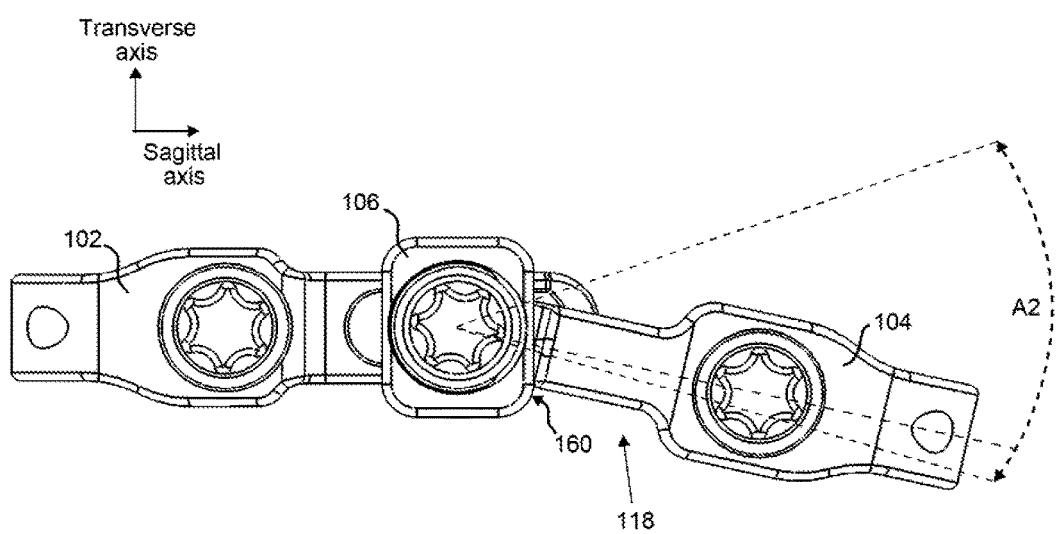

Referring now also to FIGS. 21 and 22, rotation of the second arm 104 relative to the first arm 102 and the collar 106 in the coronal plane is shown. The second arm 104 may rotate within the collar 106 about the head 136. The head 136 may freely rotate within the cavity formed by the channel 122 and the recessed portion 178 of the setscrew 172 similar to a ball joint. The second arm 104 may rotate through an angle A2. The rotational position of the second arm 104 may be limited by engagement of a portion of the second end 118 with the second transverse portion 160 of the collar 106.

Figure 23:
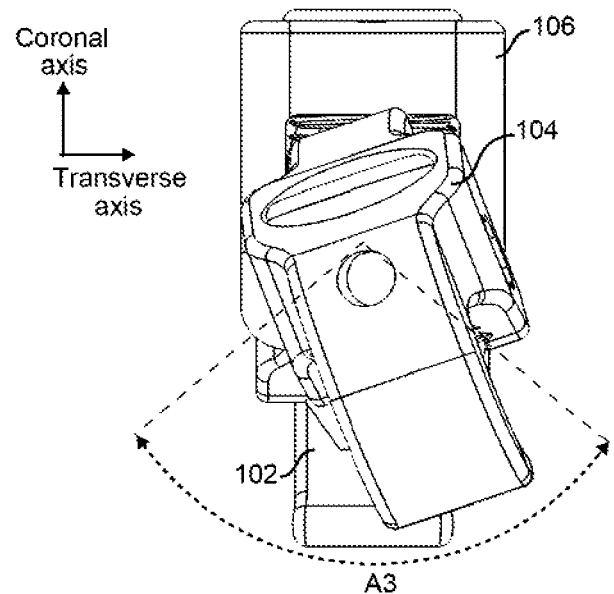
Figure 24:
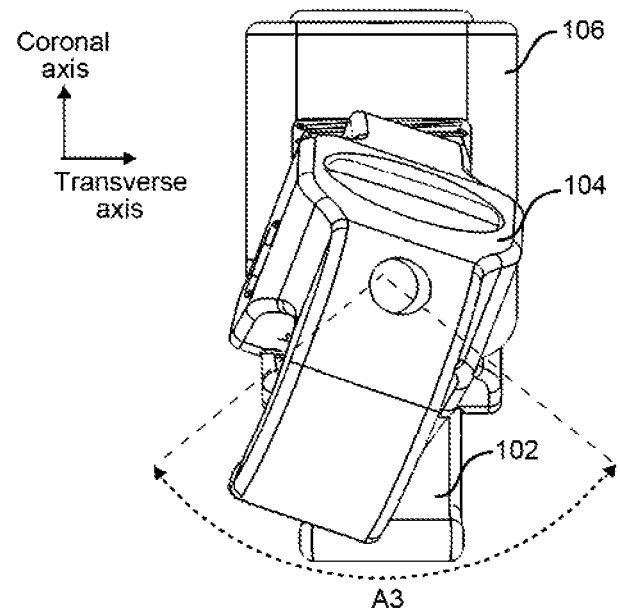
Figure 25:
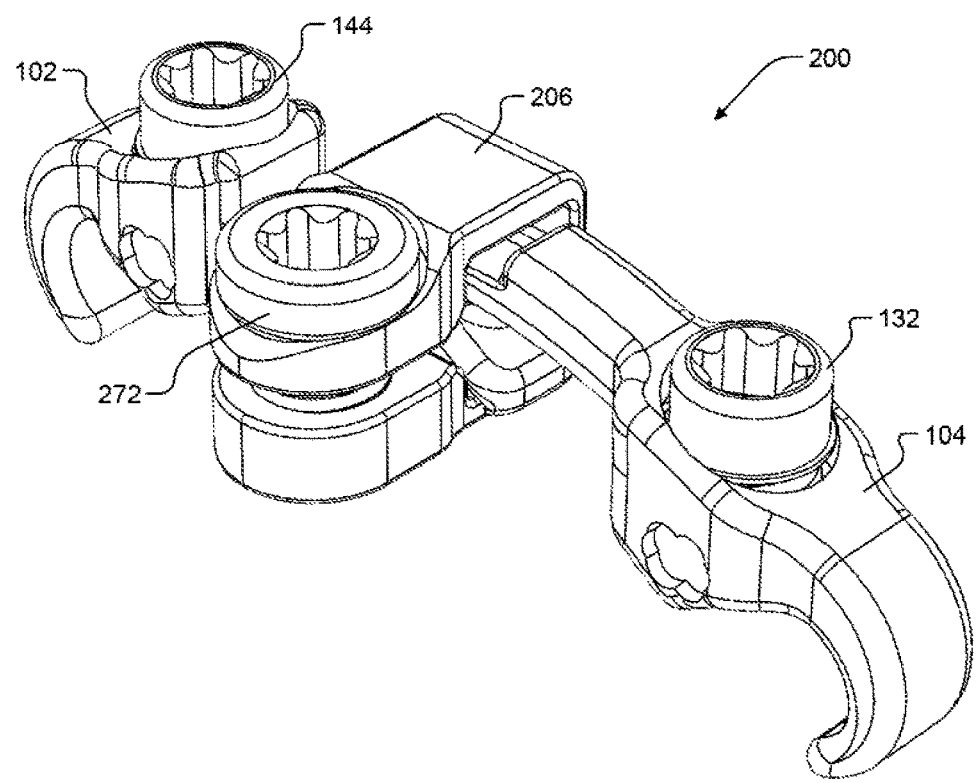
FIG. 25 is a perspective view of another exemplary apparatus for connecting surgical rods according to the principles of the present disclosure.

Referring now also to FIGS. 23 and 24, rotation of the second arm 104 relative to the first arm 102 and the collar 106 in the sagittal plane is shown. The second arm 104 may rotate within the collar 106 about the head 136. The head 136 may freely rotate within the cavity formed by the channel 122 and the recessed portion 178 of the setscrew 172 similar to a ball joint. The second arm 104 may rotate through an angle A3. The rotational position of the second arm 104 may be limited by engagement of a portion of the second end 118 with the second transverse portion 160 of the collar 106.

The crosslink 100 may be used to link a pair of alignment rods to provide additional strength and rigidity to the fixation construct. For example, the first end 108 of the first arm 102 may be attached to a first alignment rod. The first hook 120 may wrap around the first alignment rod and the first setscrew 132 may be tightened. The second end 110 of the first arm 102 may slide inside the collar 106 to adjust the overall length of the crosslink 100 and enable the first end 114 of the second arm 104 to reach the second alignment rod. The first end 114 of the second arm 104 may be attached to a second alignment rod. The second hook 134 may wrap around the second alignment rod and the second setscrew 144 may be tightened. The second end 116 of the second arm 104 may slide inside the collar 106 and rotate to adjust the angle of engagement between the second hook 134 and the second alignment rod. The second end 116 may rotate in three planes.

Once the arms 102 and 104 of the crosslink 100 have been positioned and the respective hooks 120 and 134 have been secured, the setscrew 172 within the collar 106 may be advanced to retain the head 136 and channel 122 within the collar 106. Adjustment of the arms 102 and 104 may continue while the setscrew 172 is loose. When the arms 102 and 104 are properly positioned, the setscrew 172 may be tightened to lock the first arm 102 and the second arm 104 in place within the collar 106.

Figure 26:
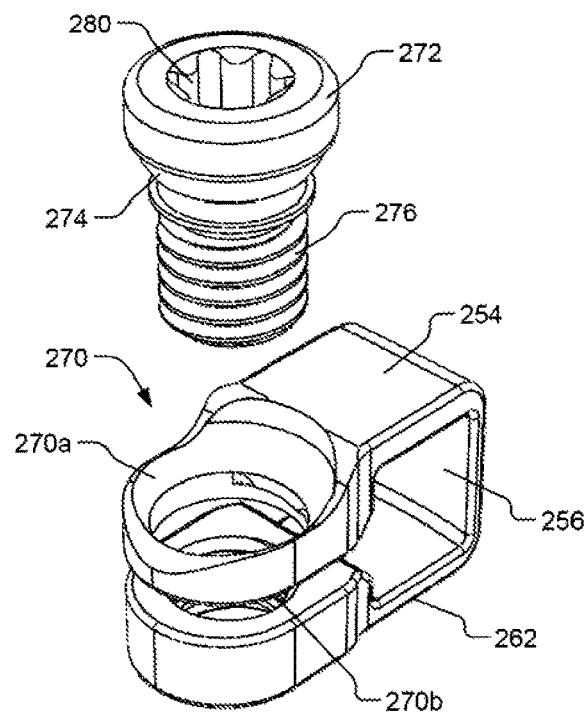
FIG. 26 is an exploded perspective view of another exemplary collar of the apparatus according to the principles of the present disclosure.
Figure 27:
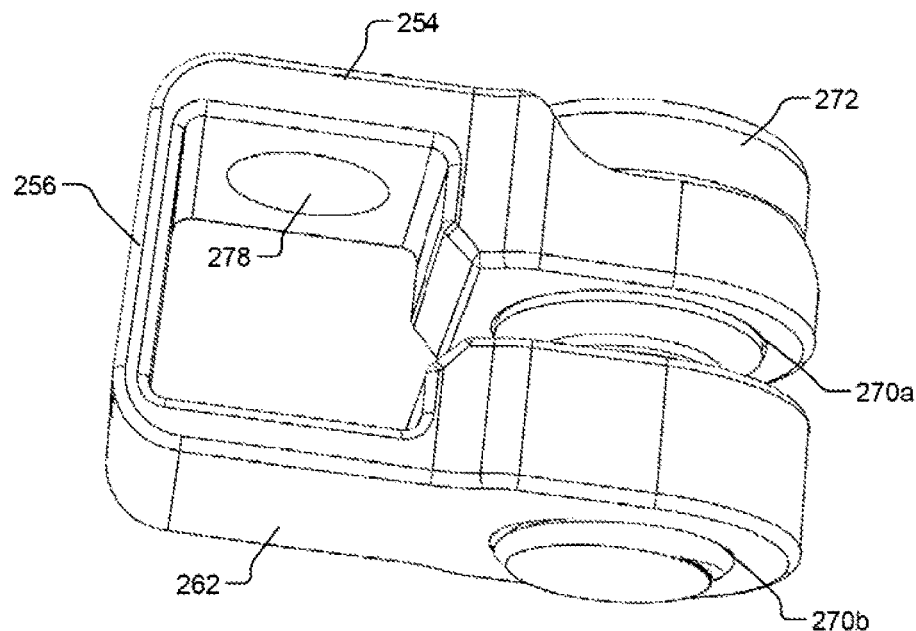
FIGS. 27 and 28 are perspective views of the collar of FIG. 26 according to the principles of the present disclosure.
Figure 28:
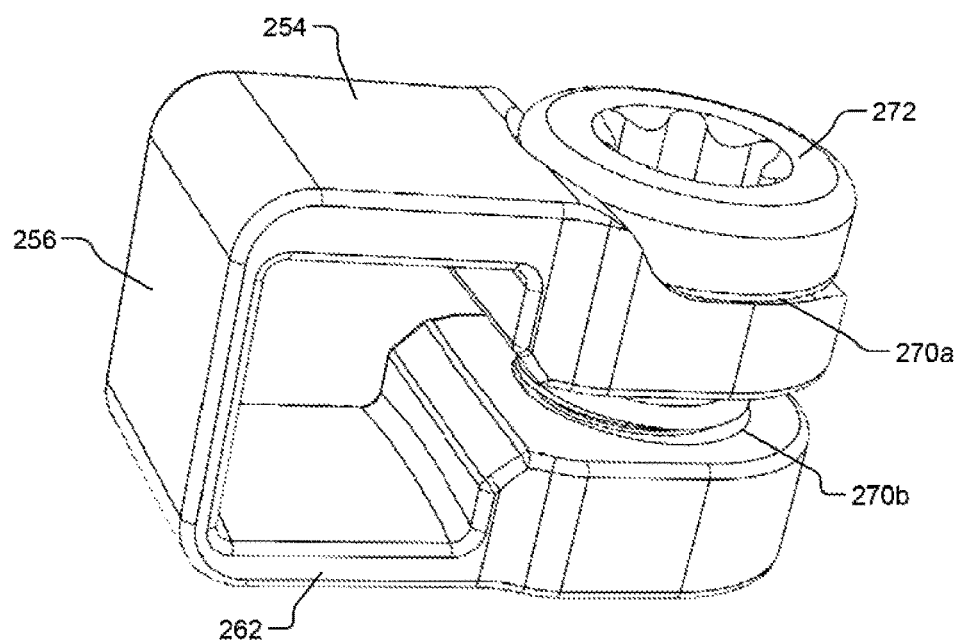

Referring now to FIGS. 26-27B, another example of a crosslink 200 includes similar features as the crosslink 100 described above. Included are the first arm 102 and the second arm 104 of the previous example in FIGS. 1-25. For example, the first arm 102 includes the first end 108 configured to couple with a first alignment rod and the second end 110 with the first engagement portion 112. The second arm 104 includes the first end 114 configured to couple with a second alignment rod and a second end 116 with a second engagement portion 118.

A clamping collar 206 replaces the collar 106. The collar 206 includes features that allow positioning of the first engagement portion 112 relative to the second engagement portion 118 in a first configuration and restricts positioning of the first engagement portion 112 relative to the second engagement portion 118 in a second configuration. For example, similar to the collar 106 in FIG. 1, the collar 206 may fit snugly around the first and second engagement portions 112 and 118 to sufficiently lock the first arm 102 in position relative to the second arm 104. And similar to the collar 106 In FIG. 2, the collar 206 may fit loosely around the first and second engagement portions 112 and 118 to enable free translation of the first arm 102 relative to the second arm 104 and the collar 206 and free rotation of the second arm 104 relative to the first arm 102 and the collar 206.

The collar 206 includes features that enable sliding engagement with the first arm 102 and rotational engagement with the second arm 104. The collar 206 includes an upper portion 254, a side portion 256, and a lower portion 262 that together form a substantially C-shaped clamp. The second end 110 of the first arm 102 may be inserted through the collar 206 and the lower surface 128 may slidably engage an interior surface of the lower portion 262. The second end 118 of the second arm 104 may be inserted through the collar 206. The second end 110 of the first arm 102 may pass through the interior of the collar 206. The lip 126 on the second end 110 may prevent the first arm 102 from sliding out of the collar 206.

The clamping collar 206 may include a third aperture 270 that receives a third setscrew 272. The third aperture 270 is offset from a transverse centerline of the crosslink 200 extending through the arms 102 and 104. The third aperture 270 may extend through the upper portion 254 and the lower portion 262. The third aperture 270 may be opposite from the side portion 256 as shown in FIG. 26. An upper portion 270a of the third aperture may include chamfered edges while a lower portion 270b of the third aperture may include a threaded section. The setscrew 272 includes a head portion 274, a threaded portion 276, and a driving feature 280. The collar 206 includes a recessed portion 278 that may include the chamfered edges. For example, the recessed portion 278 may include concave section having radius similar to the radius R1 of the semispherical head 136a. The recessed portion 278 may include a conical shaped section configured to receive the semispherical head 136a.

The setscrew 272 may be advanced through the third aperture 270 to clamp the upper portion 254 and lower portion 262 around the ends of the first arm 102 and the second arm 104. Tightening the setscrew 272 increases clamping forces on the semi-spherical portions 136 of the end of the second arm 104 and forces the end into the channel 122 of the first arm 102.

Example embodiments of the methods and systems of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

The invention claimed is:

1. An apparatus for connecting surgical rods, comprising:
   a first arm having a first length extending along a first longitudinal axis that terminates in a first free end configured to couple with a first rod and a second end with a first engagement portion having a curved channel disposed in an upper surface of the first engagement portion and a lower surface opposite the upper surface, the curved channel extending along the first longitudinal axis a predetermined length, the lower surface being generally planar;
   a second arm having a second length extending along a second longitudinal axis that terminates in a second free end configured to couple with a second rod and a second end with a second engagement portion comprising a first hemispherical portion with a first radius and a second hemispherical portion with a second radius, the second radius being greater than the first radius, configured to slidably move along the curved channel and rotatable about the curved channel; and
   a collar with a passageway having a lower portion, the lower portion having a generally planar surface so as to be slidably engaged with the lower surface of the first engagement portion and allow translation of the first arm relative to the collar along the first longitudinal axis and that engages the first hemispherical portion to allow rotation of the second arm relative to the collar in at least two planes and to prevent translation of the second arm relative to the collar along the second longitudinal axis; and an adjustment member within an aperture of the collar that adjusts a clamping force on the first engagement portion and the second engagement portion to increase an amount of friction between at least one of the first engagement portion and the passageway, the first hemispherical portion and the passageway so as to fix the first hemispherical portion to a desired position along the predetermined length of the curved channel, and wherein the adjustment member includes a concave inner surface having a radius similar to the first radius of the first hemispherical portion.

2. The apparatus of claim 1, wherein the first engagement portion terminates in a lip on the lower surface.

3. The apparatus of claim 2, wherein the lip of the first arm engages the lower portion of the collar to retain the first arm within the passageway.

4. The apparatus of claim 1, wherein the second arm further comprises a pair of flat surfaces adjacent to the first hemispherical portion and that engages the passageway to restrict rotation about the second longitudinal axis of the second arm.

5. The apparatus of claim 1, wherein the second hemispherical portion translates within the curved channel to adjust an overall length of the apparatus.

6. The apparatus of claim 1, wherein the second arm rotates about the second longitudinal axis.

7. The apparatus of claim 1, wherein the second arm pivots about a common axis extending through the first hemispherical portion and the second hemispherical portion.

8. The apparatus of claim 1, further comprising chamfered edges around the aperture in an upper surface of the collar and a threaded section in the aperture of a lower portion to receive threads of the adjustment member.

9. The apparatus of claim 1, further comprising a first rod aperture in the first free end configured to receive a first rod setscrew to couple a first hook formed in the first free end with the first rod.

10. The apparatus of claim 1, further comprising a second rod aperture in the second free end configured to receive a second rod setscrew to couple a second hook formed in the second free end with the second rod.

11. An apparatus for connecting surgical rods, comprising:

a first arm having a first length extending along a first longitudinal axis that terminates in a first free end configured to couple with a first rod and a second end with a first engagement portion having a curved channel disposed in an upper surface of the first engagement portion and a lower surface opposite the upper surface, the curved channel extending along the first longitudinal axis a predetermined length, the lower surface being generally planar;

a second arm having a second length extending along a second longitudinal axis that terminates in a second free end configured to couple with a second rod and a second end with a second engagement portion comprising a first hemispherical portion with a first radius and a second hemispherical portion with a second radius, the second radius being greater than the first radius, configured to slidably move along the first longitudinal axis of the curved channel and rotatable about the curved channel; and a collar with a passageway having a lower portion, the lower portion having a generally planar surface so as to be slidably engaged with the lower surface of the first engagement portion and allow translation of the first arm relative to the collar along the first longitudinal axis and that engages the first hemispherical portion to allow rotation of the second arm relative to the collar in at least two planes and to prevent translation of the second arm relative to the collar along the second longitudinal axis; and wherein the collar includes a concave inner surface having a radius similar to the fist radius of the first hemispherical portion and an adjustment member within an aperture of the collar that adjusts a clamping force on the first engagement portion and the second engagement portion to increase an amount of friction between at least one of the first engagement portion and the passageway, the first hemispherical portion and the passageway so as to fix the first hemispherical portion to a desired position along the predetermined length of the curved channel.

12. The apparatus of claim 11, wherein the passageway includes the concave inner surface configured to retain the first hemispherical portion.

13. The apparatus of claim 11, wherein the aperture in the collar extends through an upper portion and a lower portion of the collar that are offset from the passageway and the first and second longitudinal axes of the first and second arms respectively.

14. The apparatus of claim 11, wherein the adjustment member extends through the aperture without contacting the first arm and the second arm.

15. The apparatus of claim 11, wherein the aperture does not intersect the passageway.

16. The apparatus of claim 11, wherein the adjustment member does not engage the first arm and the second arm.

* * * * *